(12) United States Patent
Armitage (10) Patent No.: US 8,436,335 B2
(45) Date of Patent: May 7, 2013

(54) DETECTING ELEMENT, DETECTING DEVICE, AND OXYGEN CONCENTRATION TEST DEVICE

(75) Inventor: Robert David Armitage, Los Altos, CA (US)

(73) Assignee: Panasonic Corporation, Osaka (JP)

( * ) Notice: Subject to any disclaimer, the term of this patent is extended or adjusted under 35 U.S.C. 154(b) by 164 days.

(21) Appl. No.: 13/125,873

(22) PCT Filed: Oct. 27, 2009

(86) PCT No.: PCT/JP2009/068371
§ 371 (c)(1),
(2), (4) Date: Apr. 25, 2011

(87) PCT Pub. No.: WO2010/050454
PCT Pub. Date: May 6, 2010

(65) Prior Publication Data
US 2011/0205530 A1    Aug. 25, 2011

(30) Foreign Application Priority Data

Oct. 29, 2008  (JP) .................................. 2008-278159

(51) Int. Cl.
*H01L 29/06*    (2006.01)
(52) U.S. Cl.
USPC ........ 257/13; 257/E31.102; 356/51; 356/437; 977/755
(58) Field of Classification Search ........ 257/13, 257/E31.102; 356/51, 437; 977/755
See application file for complete search history.

(56) References Cited

U.S. PATENT DOCUMENTS

| | | |
|---|---|---|
| 6,331,438 B1 | 12/2001 | Aylott et al. |
| 2006/0110835 A1 | 5/2006 | Gohil |
| 2006/0123900 A1 | 6/2006 | Sugita |
| 2008/0218757 A1 | 9/2008 | Sugita |
| 2010/0207136 A1 | 8/2010 | Armitage et al. |
| 2011/0012168 A1 | 1/2011 | Armitage |
| 2011/0062453 A1 | 3/2011 | Armitage |

FOREIGN PATENT DOCUMENTS

| | | |
|---|---|---|
| JP | 2002-168783 | 6/2002 |
| JP | 2003-515163 | 4/2003 |
| JP | 2004-151093 | 5/2004 |
| JP | 2007-232716 | 9/2007 |
| JP | 2008-522163 | 6/2008 |

*Primary Examiner* — Tan N Tran
(74) *Attorney, Agent, or Firm* — Greenblum & Bernstein, P.L.C.

(57) ABSTRACT

Provided is a detecting element that detects a parameter for a predetermined gas or liquid in a surrounding atmosphere by being excited by excitation light and generating light corresponding to the surrounding atmosphere, the detecting element including: a substrate; and nanoscale crystal structures formed on the substrate and constituted by a compound semiconductor light emitting element having a heterostructure well layer, wherein when the nanoscale crystal structures adsorb atoms or molecules of the predetermined gas or liquid, there is distortion of a band of a structure with a smaller bandgap width in the well layer, this distortion brings about a change in transition energy, and this change brings about a change in at least one of an intensity and a wavelength of light generated by the well layer, thereby indicating the parameter for the gas or the liquid.

12 Claims, 7 Drawing Sheets

DETECTING ELEMENT, DETECTING DEVICE, AND OXYGEN CONCENTRATION TEST DEVICE

TECHNICAL FIELD

This invention relates to a detecting element, a detecting device, and an oxygen concentration test device that are suitable as a gas detecting element, a gas detector, or the like.

BACKGROUND ART

Various optical chemical sensors have been devised in recent years. There is high commercial demand for these sensors. For instance, there is high demand for optical oxygen sensors in the fields of foods and chemicals that are not supposed to be oxidized. There is also heavy demand for oxygen detection in industrial fields such as semiconductors and biology. The optical oxygen sensor disclosed in Patent Document 1 is a first example of prior art related to optical chemical sensors that have been invented so far.

With this prior art, an organic dye compound that receives and emits light is dispersed in an oxygen-permeable polymer. This makes use of the fact that the presence of oxygen reduces the emission brightness, so the oxygen concentration can be detected from a change in the emission brightness. This chemical sensor can be used repeatedly, and has good quantitative sensitivity, so it has been put to use in chemical laboratories.

A second example of prior art that has been widely used in the past is an oxygen sensor that makes use of a chemical substance whose color changes in the presence of oxygen. This sensor is inexpensive and easy to manufacture, and has been used in food packaging and so forth.

Because this second example of oxygen sensor prior art is inexpensive, can be sealed right into a food package. However, it is lacking in terms of quantitative sensitivity, so all that can be evaluated is whether the seal of the package has been broken and there is the risk that the food has been oxidized. Also, because it is used in the above-mentioned applications, it is not expected to be reused, and it is premised on a single use and a one-way chemical change. Also, since it contains organic matter, it cannot be used in high-temperature environments.

In this respect, the first prior art example, as mentioned above, can be used repeatedly and has good quantitative sensitivity, but cannot be used in high-temperature environments because it contains organic matter.

CITATION LIST

Patent Literature

Patent Document 1: Japanese Patent Application Laid-open No. 2002-168783

SUMMARY OF THE INVENTION

It is an object of the present invention to provide a detecting element, a detecting device, and an oxygen concentration test device that can be used in a high-temperature environment.

The detecting element pertaining to a first aspect of the present invention is a detecting element that detects a parameter for a predetermined gas or liquid in a surrounding atmosphere by being excited by excitation light and generating light corresponding to the surrounding atmosphere, the detecting element including: a substrate; and nanoscale crystal structures formed on the substrate and constituted by a compound semiconductor light emitting element having a heterostructure well layer, wherein when the nanoscale crystal structures adsorb atoms or molecules of the predetermined gas or liquid, there is distortion of a band of a structure (material) with a smaller bandgap width in the well layer, this distortion brings about a change in transition energy (apparent bandgap width), and this change brings about a change in at least one of an intensity and a wavelength of light generated by the well layer, thereby indicating the parameter for the gas or the liquid.

The detecting element having this constitution is excited by excitation light and emits light corresponding to the surrounding atmosphere, and thereby detects a parameter (such as type, concentration, temperature, or humidity) for a predetermined gas or liquid in the surrounding atmosphere. The detecting element comprises nanoscale crystal structures that are formed on the substrate and are constituted by a compound semiconductor light emitting element having a heterostructure well layer. The nanoscale crystal structures are in the form of columns or sheets (walls), and at least the thinnest portion should be on the nanoscale. When the compound semiconductor light emitting element receives excitation light and emits light, if the nanoscale crystal structures adsorb atoms or molecules of the predetermined gas or liquid (the test substance), there will be distortion in the structure (material) with the smaller bandgap width in the well layer, this distortion will bring about a change in the transition energy (apparent bandgap width), and this change brings about a change in the intensity (brightness) and wavelength of light generated by the well layer. A specific parameter of the gas or liquid (test substance) is detected from a change in at least one of the intensity and the wavelength.

Because of their high growth temperature, the nanoscale crystal structures constituted by the compound semiconductor light emitting element can be used in high-temperature environments, and furthermore they are stable (undergo little corrosion or modification) with respect to many gases and liquids (test substances), so they can be used repeatedly. In particular, there is little degradation in sensitivity when the parameter is detected from the wavelength, so the detection is extremely quantitative and there is no need for calibration.

The detecting device pertaining to a second aspect of the present invention is a detecting device that detects a parameter for a predetermined gas or liquid, including: a detecting element in which nanoscale crystal structures constituted by a compound semiconductor light emitting element having a heterostructure well layer are provided on a substrate; excitation means for causing the compound semiconductor light emitting element to emit light; and detection means for receiving the light emitted from the compound semiconductor light emitting element and detecting at least one of an intensity and a wavelength of this light, wherein when the nanoscale crystal structures adsorb atoms or molecules of the predetermined gas or liquid, there is distortion of a band of a structure (material) with a smaller bandgap width in the well layer, this distortion brings about a change in transition energy (apparent bandgap width), and the detection means detects a change in at least one of an intensity and a wavelength of light generated by the well layer, thereby detecting the parameter for the gas or the liquid.

With this constitution, with a detecting device that detects a specific parameter, such as the type, concentration, temperature, or humidity, for a gas or liquid (test substance), the detecting element comprises nanoscale crystal structures constituted by a compound semiconductor light emitting element having a heterostructure well layer. The nanoscale crystal structures are in the form of columns or sheets (walls), and at least the thinnest portion should be on the nanoscale. When the compound semiconductor light emitting element is excited by the excitation means and emits light, if the nanoscale crystal structures adsorb atoms or molecules of the predetermined gas or liquid (the test substance), there will be distortion in the structure (material) with the smaller bandgap width in the well layer, this distortion will bring about a change in the transition energy (apparent bandgap width), and this change brings about a change in the intensity (brightness) and wavelength of light generated by the well layer. The detection means detects at least one of these changes. At least one of the intensity and the wavelength is measured ahead of time and is then contrasted with the parameter for the predetermined gas or liquid (test substance), and the actual parameter value is calculated.

Because of their high growth temperature, the nanoscale crystal structures constituted by the compound semiconductor light emitting element can be used in high-temperature environments, and furthermore they are stable (undergo little corrosion or modification) with respect to many gases and liquids (test substances), so they can be used repeatedly. In particular, there is little degradation in sensitivity when the parameter is detected from the wavelength, so the detection is extremely quantitative and there is no need for calibration.

The oxygen concentration test device pertaining to a third aspect of the present invention includes: a light emitting element that includes nanoscale crystal structures constituted by a compound semiconductor having a GaN/InGaN heterostructure well layer, and whose emission wavelength and brightness vary with an oxygen concentration in an atmosphere; a supply component that supplies excitation energy to the light emitting element; and a light receiving component that receives light emitted from the light emitting element by the excitation energy supplied from the supply component.

With this constitution, the oxygen concentration test device can be used in high-temperature environments.

DESCRIPTION OF EMBODIMENTS

First Embodiment

Figure 1:
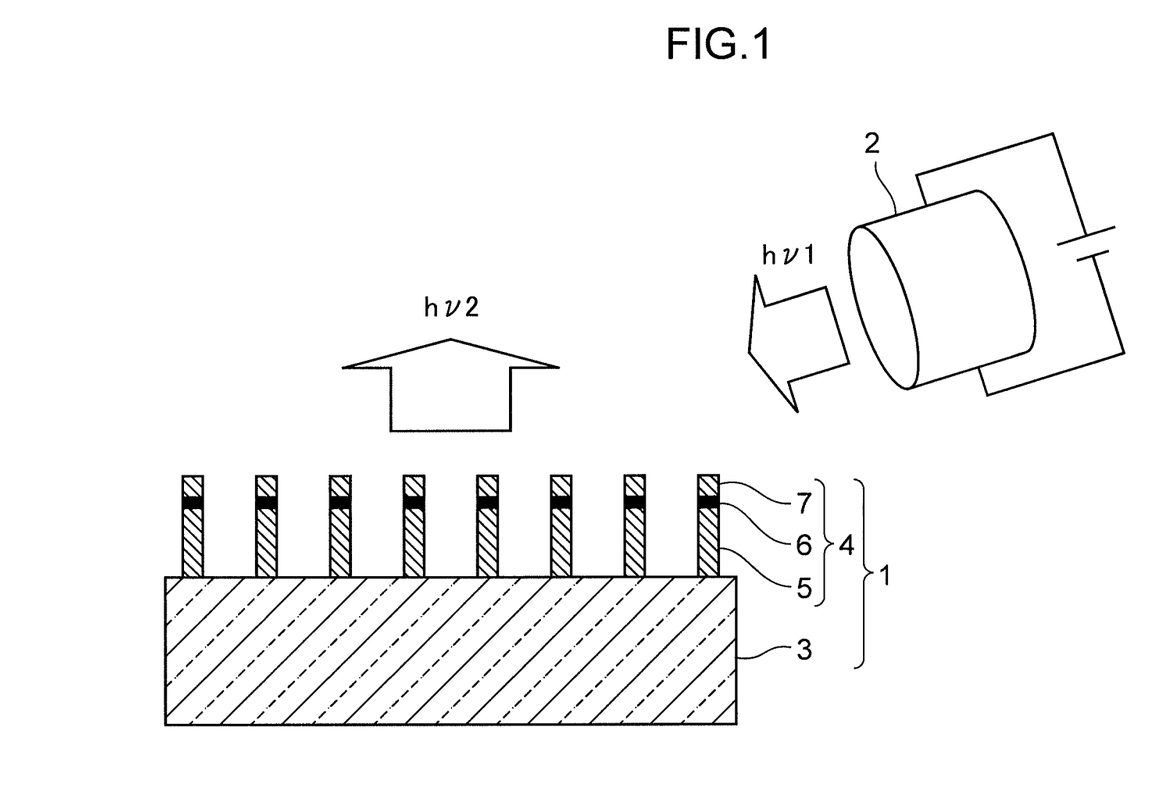
FIG. 1 is a cross section of the structure of an oxygen concentration test chip, which is the detecting element pertaining to a first embodiment of the present invention.
Figure 2:
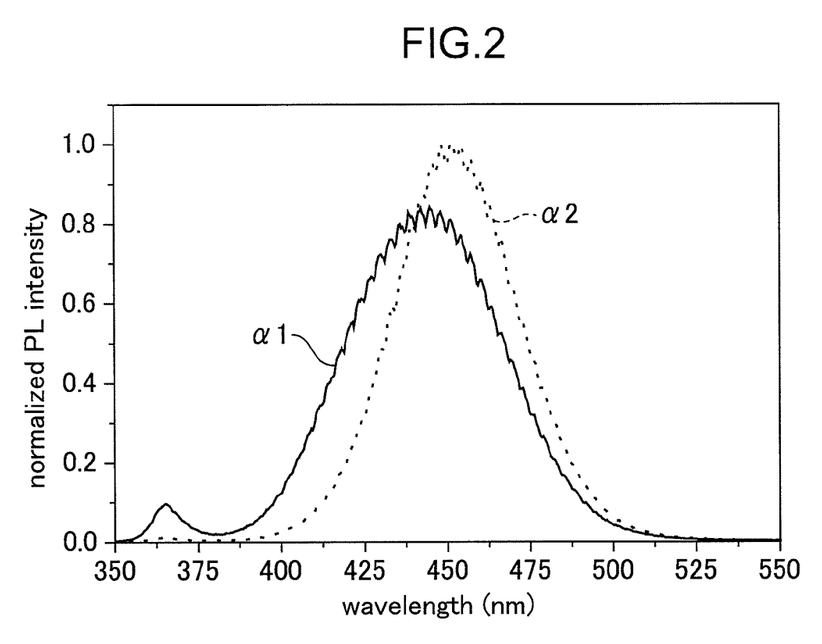
FIG. 2 is a graph of the emission spectrum for GaN nanocolumns with respect to the ultraviolet excitation light.

FIG. 1 is a cross section of the structure of an oxygen concentration test chip 1, which is the detecting element pertaining to a first embodiment of the present invention. This chip 1 emits light with an energy hv2 when irradiated with excitation light with an energy hv1 from a UV light source 2. The wavelength of this light changes as shown in FIG. 2 according to the oxygen concentration, and this can be utilized to detect the approximate oxygen concentration.

The chip 1 comprises an array of GaN nanocolumns 4 formed on a sapphire substrate 3. Each of the GaN nanocolumns 4 comprises an n-type GaN layer 5, a GaN/InGaN heterostructure well layer (light emitting layer) 6, and a p-type GaN layer 7. The GaN nanocolumns 4 can be produced as follows, for example.

Figure 7A:
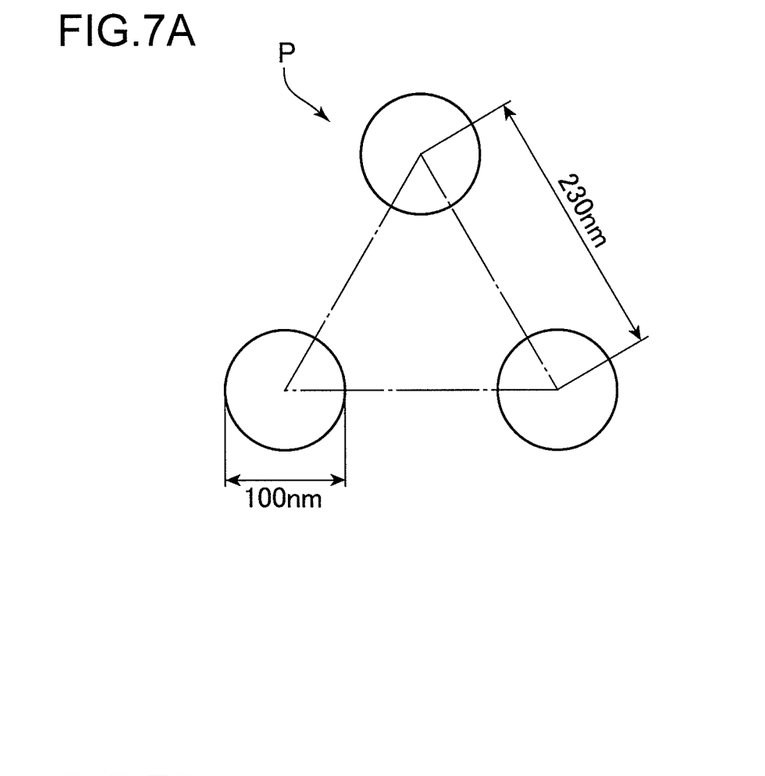
FIG. 7A is a plan view of the basic unit of a nickel thin-film pattern P.
Figure 7B:
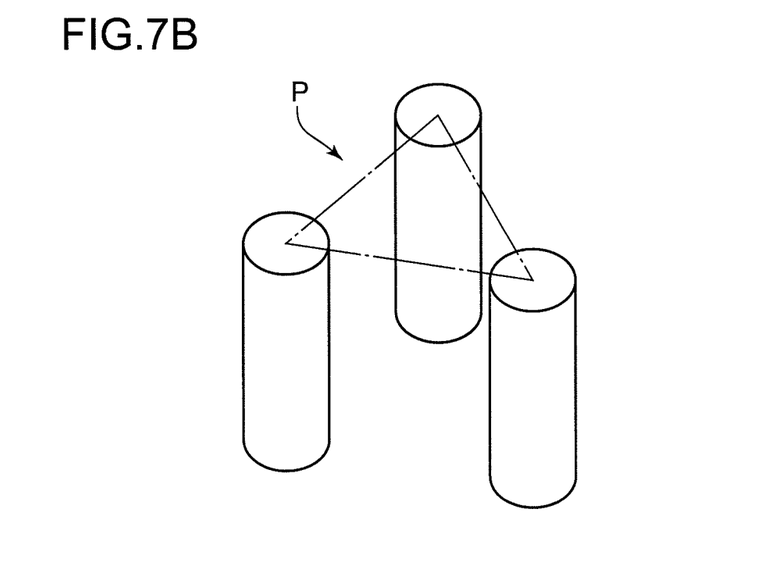
FIG. 7B is a three-dimensional view of the basic unit of a nickel thin-film pattern P.

First, a nickel thin-film that will serve as a catalyst material layer is deposited in a thickness of 5 nm by electron beam vapor deposition on the sapphire substrate 3. The nickel thin-film is formed in a nickel thin-film pattern in the form of a diffraction lattice pattern made up of two-dimensional photonic crystals, using an ordinary lithography technique and a dry etching technique such as argon ion etching. As shown in FIG. 7, this nickel thin-film pattern P has a basic unit with a column diameter of 100 nm and triangular shape that is 230 nm on one side. This product is then put in an MOCVD device and the temperature is set to 900° C., and in this state trimethylgallium ($Ga(CH_3)_3$) and ammonia ($NH_3$) are supplied as gases for the growth of GaN crystals, which results in gallium and nitrogen being adsorbed to the surface of the nickel thin-film pattern. The gallium raw material for the GaN crystal growth is trimethylgallium, and the nitrogen raw material is ammonia. The adsorbed gallium and nitrogen atoms are incorporated into the nickel thin-film, diffuse into this nickel thin-film, and reach the boundary with the substrate 1, where they bond to each other and form GaN single crystals. Meanwhile, the gallium and nitrogen deposited directly on the sapphire substrate 3 cannot bond to each other, and therefore no GaN single crystals are formed on the sapphire substrate 3. Thus, GaN single crystals grow only between the nickel thin-film and the sapphire substrate 3.

This state is maintained for a specific length of time to form columnar crystals of GaN with a length of approximately 1 μm, that is, the GaN nanocolumns 4. A nickel thin-film, on which is arranged a pattern of two-dimensional photonic crystals with the column diameter that was first determined, is present at the top of these GaN nanocolumns 4. If the growth conditions are maintained properly, the GaN nanocolumns 4 will continue growing at the same diameter in the predetermined locations. In the growth of these GaN nanocolumns 4, silane ($SiH_4$), trimethylindium ($In(CH_3)_3$), biscyclopentadienyl magnesium ($Cp_2Mg$), or the like can be supplied to form the n-type GaN layer 5, the well layer light emitting layer 6, and the p-type GaN layer 7. Silane is a silicon raw material for forming an n-type layer, trimethylindium is an indium raw material for forming a quantum well, and biscyclopentadienyl magnesium is a magnesium raw material for forming a p-type layer.

In the first embodiment, GaN is used as an example of the material of the nanocolumns 4, but this is not the only option, and any compound semiconductor including oxides, nitrides, oxynitrides, or the like can be used. Also, a metalorganic chemical vapor deposition (MOCVD) device was used to grow the columns 4, but a molecular beam epitaxy (MBE) device, a hydride vapor phase epitaxy (HVPE) device, or the like may be used instead to grow the columns 4.

Figure 3A:
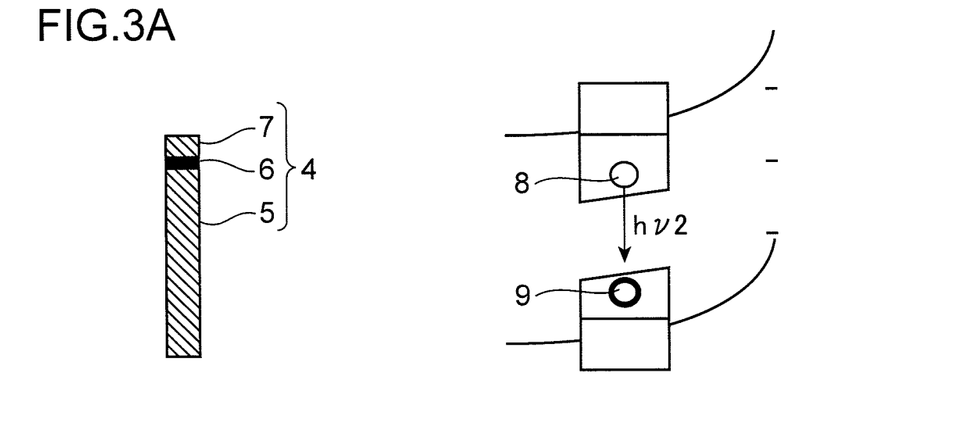
FIG. 3A is a diagram illustrating the operating principle behind the oxygen concentration test chip shown in FIG. 1 when no oxygen gas is present.
Figure 3B:
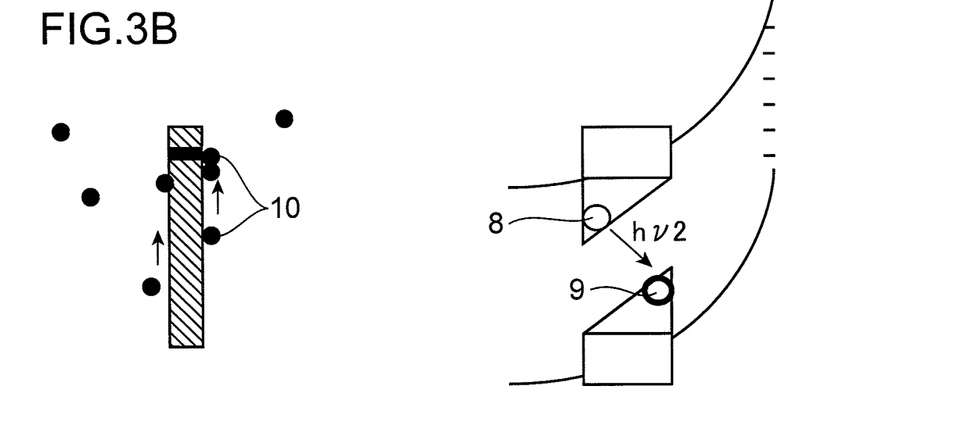
FIG. 3B is a diagram illustrating the operating principle behind the oxygen concentration test chip shown in FIG. 1 when oxygen gas is present.

FIGS. 3A and 3B are diagrams illustrating the operating principle behind the oxygen concentration test chip 1 constituted as discussed above. FIG. 3A shows the GaN nanocolumns 4 and the energy band thereof when there is no oxygen gas (test substance). As mentioned above, the GaN nanocolumns 4 comprise the n-type GaN layer 5, the GaN/InGaN heterostructure well layer 6, and the p-type GaN layer 7. Here, the energy band graph of the well layer 6 has a structure that is generally inclined with respect to a flat band because of the surface level and internal piezo resistance. When in this state external excitation light generates carriers so that and electrons 8 and holes 9 are supplied to the well layer 6, the two bond over a certain buffering time, and light equivalent to a bandgap energy hv2 is generated.

Next, FIG. 3B shows the GaN nanocolumns 4 when oxygen gas 10 (the test substance) is present, and the energy band thereof. The energy band graph of the well layer 6 here changes to a structure that is more markedly inclined with respect to the flat band than when the oxygen gas 10 is not present, due to the adsorption and ionization of the oxygen gas 10 at the surface of the GaN nanocolumns 4, in addition to the surface level and internal piezo resistance. Accordingly, when external excitation light generates carriers so that and electrons 8 and holes 9 are supplied to the well layer 6, the electrons 8 and holes 9 bond and generate the energy hv2, which differs from the energy hv2 generated when no oxygen gas 10 has been adsorbed. Therefore, light of different wavelengths is released when the oxygen gas 10 is adsorbed and when the oxygen gas 10 is not adsorbed. In general, the wavelength when the oxygen gas 10 is adsorbed is shifted more to the long wavelength side than when no oxygen gas 10 is adsorbed. The amount of this wavelength shift can be used to detect the concentration of the oxygen gas 10.

FIG. 2 is a graph of the emission spectrum of the GaN nanocolumns 4 corresponding to UV excitation light (360 nm). The horizontal axis is the wavelength, and the vertical axis is the standardized emission intensity (brightness). α1 in the graph is data obtained in a vacuum (no oxygen), and α2 is data obtained in an atmosphere filled with the oxygen gas 10. As discussed above, it can be seen that in an oxygen atmosphere the emission spectrum is shifted to the long wavelength side (440→450 nm). These spectral ranges are blue visible light, so the difference in the spectra can be easily recognized by eye.

As above, the oxygen concentration test chip 1 in the first embodiment is excited by excitation light from the UV light source 2, and generates light with a wavelength and brightness corresponding to the oxygen concentration. This chip 1 comprises the GaN nanocolumns 4 having the heterostructure well layer 6 on the sapphire substrate 3. When the GaN nanocolumns 4 adsorb oxygen molecules or atoms, there is distortion in the band of the structure (material) with the smaller bandgap width in the heterostructure well layer 6, this distortion brings about a change in the transition energy (the apparent bandgap width), and this change brings about a change in at least one of the intensity (brightness) and the wavelength of the light generated by the well layer 6, and this indicates the oxygen concentration.

Because of their high growth temperature, the GaN nanocolumns 4 can be used in high-temperature environments (at least 500° C.), and furthermore they are stable (undergo little corrosion or modification) with respect to the oxygen gas 10, so they can be used repeatedly. In particular, there is little degradation in sensitivity when the oxygen concentration is detected by utilizing the wavelength (color), so the detection is extremely quantitative and there is no need for calibration.

Also, with the oxygen concentration test chip 1 pertaining to the first embodiment, the light generated by the well layer 6 (energy hv2) is set to the region of visible light as mentioned above, so whether or not the oxygen gas 10 is present, and its concentration, can be readily discerned by the human eye.

Second Embodiment

Figure 4:
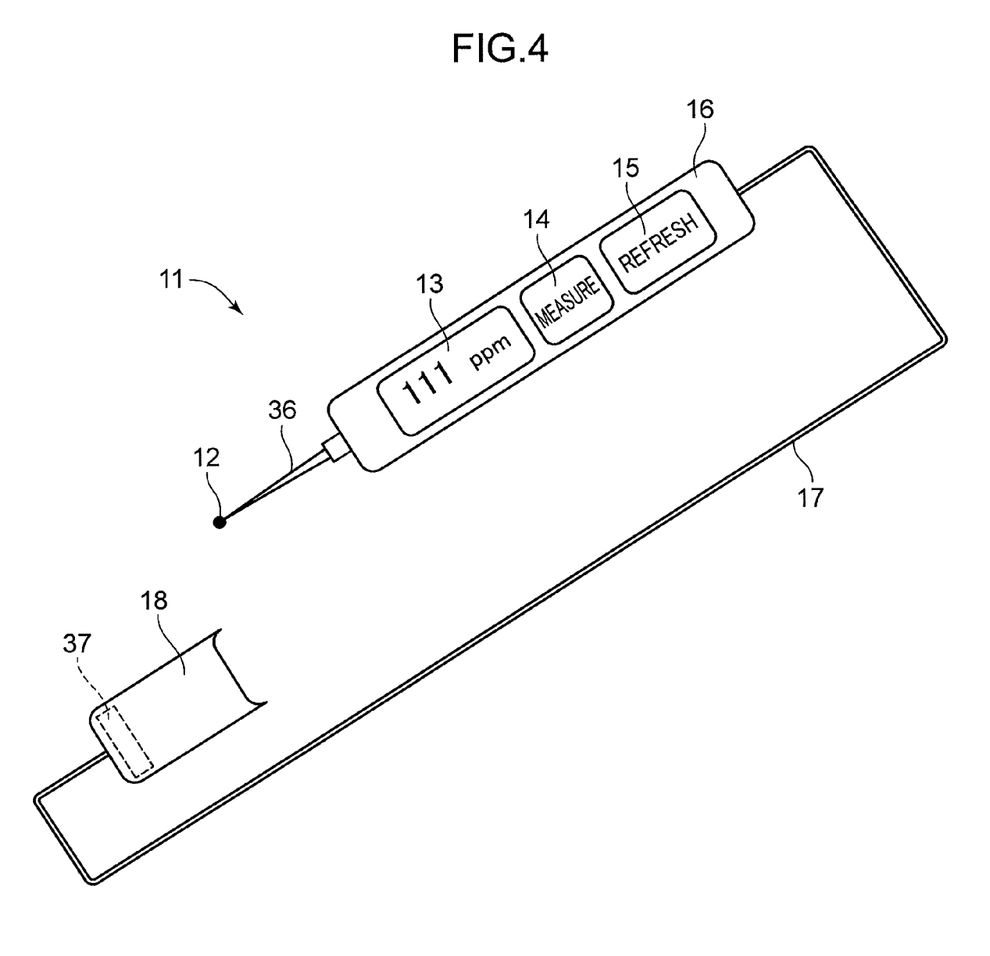
FIG. 4 is a diagram of the structure of an oxygen concentration sensor, which is the detecting device pertaining to a second embodiment of the present invention.

FIG. 4 is a diagram of the structure of an oxygen concentration sensor 11 (detecting device) pertaining to a second embodiment of the present invention. This oxygen concentration sensor 11 is a portable type of detecting device that is made in the shape of a pen. An oxygen concentration test chip 12 is provided to the pen tip of the sensor 11. A display component 13 that displays measurement results, a measurement button 14, and a refresh button 15 (discussed below) are provided to the main body 16 of the sensor 11. A cap 18 is fitted to the main body 16 to protect the chip 12. The main body 16 and the cap 18 are connected by a cable 17.

Figure 5:
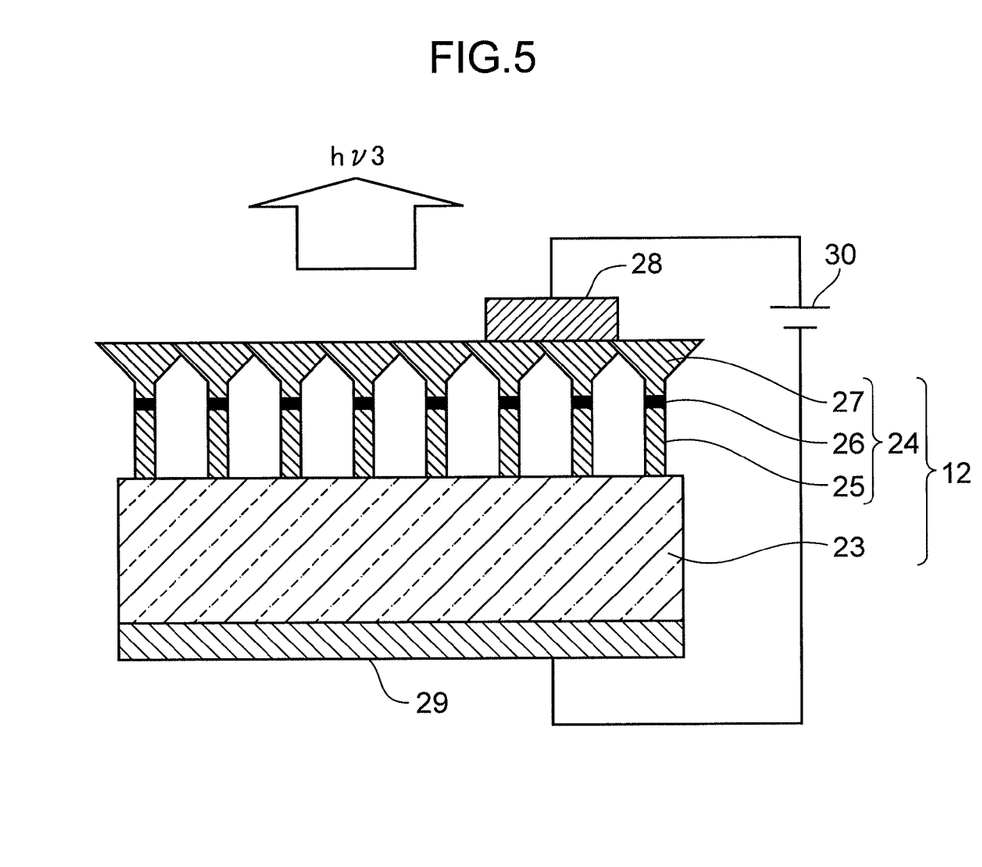
FIG. 5 is a cross section of the structure of an oxygen concentration sensor, which is the detecting device pertaining to a second embodiment of the present invention.

The chip 12 that is favorable for this sensor 11 is constituted as shown in FIG. 5, for example. An array of GaN nanocolumns 24 is formed on a silicon substrate 23. The silicon substrate 23 and the GaN nanocolumns 24 are both electroconductive. Each of the GaN nanocolumns 24 comprises an n-type GaN layer 25, a GaN/InGaN heterostructure well layer (light emitting layer) 26, and a p-type GaN layer 27. The diameter of the upper part of the p-type GaN layer 27 is increased so that it comes into electrical contact with the adjacent p-type GaN layer 27. Consequently, the shape of the p-type GaN layer 27 is planar when viewed from above. To supply carriers to the well layer 26, a p-type electrode 28 is connected on the p-type GaN layer 27, an n-type electrode 29 is connected via the silicon substrate 23 to the n-type GaN layer 25, and these electrodes 28 and 29 are connected to an external DC power supply 30. Supplying carriers generates light that has energy hv3 equivalent to the bandgap energy of the heterostructure well layer 26. The wavelength of this light changes due to the principle described through reference to FIG. 3, the cause of which is the difference in the concentration of oxygen molecules and atoms adsorbed to the surface of the GaN nanocolumns 24. The main body 16 shown in FIG. 4 calculates the oxygen concentration on the basis of the above-mentioned change in wavelength, and displays this value on the display component 13. The GaN nanocolumns 24 are produced by the same method as in the first embodiment.

Figure 6:
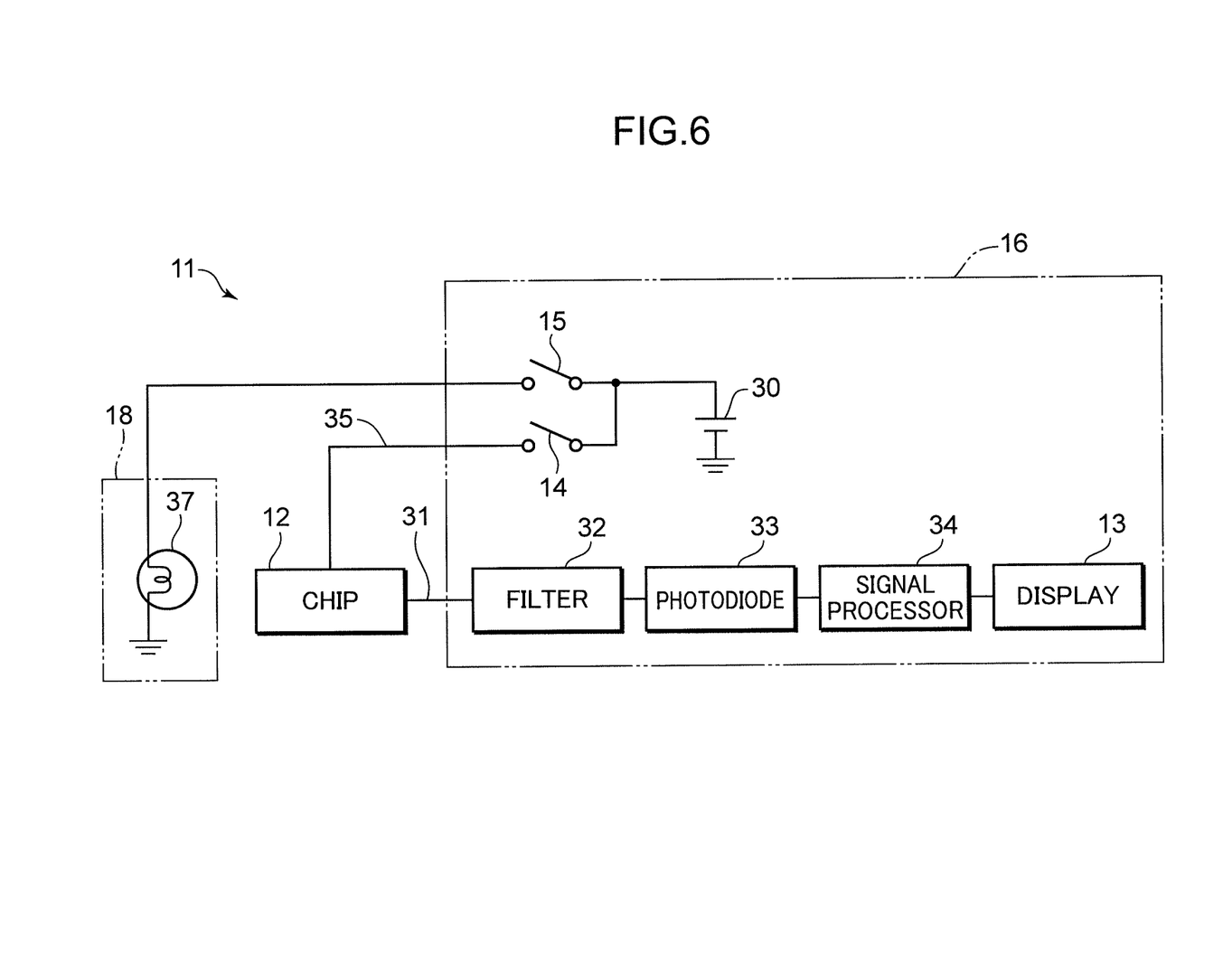
FIG. 6 is a block diagram of the electrical structure of the oxygen concentration sensor in FIG. 4.

FIG. 6 is a block diagram of the electrical configuration of the sensor 11. When the measurement button 14 disposed on the main body 16 is pressed, current flows from the DC power supply 30 (an excitation means provided inside the main body 16) to the chip 12, and the chip 12 emits light. This light goes through an optical fiber 31 and is dispersed by filters 32 in the main body 16, after which it is photoelectrically converted by corresponding photodiodes 33. The above-mentioned filters 32 and photodiodes 33 (detection means) are provided in at least three types, namely, a red filter 32 and photodiode 33, a green filter 32 and photodiode 33, and a blue filter 32 and photodiode 33, in order to disperse the light of the GaN nanocolumns 24. A signal processor 34 (computation means) computes the spectral distribution from the output of the photodiodes 33, compares this spectral distribution with oxygen concentration data measured and stored ahead of time, and calculates the actual oxygen concentration, which is displayed on the display component 13 as shown in FIG. 4.

With the oxygen concentration test chip 1 in the first embodiment, the user determined the oxygen concentration by looking at the color (wavelength) of the emitted light, so the oxygen concentration could only be ascertained in rough terms. In the second embodiment, on the other hand, the oxygen concentration is displayed, so the oxygen concentration can be precisely quantified. The constitution in the second embodiment can also be used in a high-temperature environment. Furthermore, since it is stable (undergoes little corrosion or modification) with respect to the oxygen gas 10, it can be used repeatedly. In particular, when a parameter is detected from the wavelength (color) as discussed above, there is little sensitivity degradation, so the detection is extremely quantitative and there is no need for calibration.

Providing the optical fiber 31 and an excitation light power line 35 allows the chip 12 to be kept away from the main body 16 that houses the rest of the structure of the sensor 11. Since the size of the chip 12 can be kept to 1 mm or less on one side, a leader 36 that houses the optical fiber 31 and the power line 35 and supports the chip 12 can be made as fine as an injection needle. This allows for easy measurement of a chemical substance in a liquid in a chemistry lab or the like. Also, the chip 12 contains no substances that are harmful to an organism, so the chip 12 can be inserted into the body.

It should also be noted that a UV lamp 37 is provided inside the protective cap 18 of the chip 12, facing the chip 12. In a state in which the cap 18 has been fitted to the main body 16, when the refresh button 15 is pressed, and preferably under reduced pressure, current flows from the DC power supply 30 to this UV lamp 37, and the UV lamp 37 is lit. When irradiated with UV rays, the atoms or molecules of oxygen or the like adsorbed to the GaN nanocolumns 24 of the chip 12 scatter, so the state can be refreshed. Consequently, the sensor 11 can always be kept in good sensitivity, and the sensor 11 can be used repeatedly, so environmental resistance is excellent and cost performance is high in this sensor.

In the above description, an example of an oxygen concentration sensor was mainly given, but it is also possible to detected $CO_2$ by providing polyethylimine (PEI), for example, to the surfaces of the GaN nanocolumns 4 and 24, and $H_2$ can be detected by providing a semi-transparent platinum layer. Furthermore, DNA can be detected by providing a semi-transparent metal film to the surfaces of the GaN nanocolumns 4 and 24. The above are examples of substances that can be detected, but what is detected with the present invention is not limited to $O_2$, $CO_2$, $H_2$, or DNA, and it should go without saying that the test substance can be any substance to which the principle of the present invention can be applied. Also, the present invention can be used to detect temperature, humidity, and liquid.

Also, in the above description the nanoscale crystal structures were described as being the GaN nanocolumns 4 and 24, that is, columnar structures, but they may instead be sheet-like (wall-like) structures. In this case, at least the thinnest portion should be on the nanoscale. However, with a given chip surface area, the surface area will be greater with nanocolumns, so they are more sensitive to the adsorption of a test substance, and yield a detecting element with higher sensitivity.

Japanese Patent Application Laid-open No. 2004-151093 discloses a sensor in which a microscopic resonator laser diode is installed to the side of a flow path. With this sensor, the resonation conditions of the microscopic resonator laser diode vary with changes in the fluid or the environment, this change brings about a change in the light outputted from the diode, and this change is detected to find a concentration or temperature. However, this sensor is only used in special applications, and is not general-purpose.

What was described in the first embodiment was the oxygen concentration test chip 1, and in the second embodiment the oxygen concentration sensor 11. As shown in FIG. 2, however, a comparison of data ($\alpha1$) obtained in a vacuum (no oxygen) and data $\alpha2$ obtained in an atmosphere filled with the oxygen gas 10 reveals that the wavelength and brightness of the light emitted by the well layer 6 varies depending on whether or not oxygen is present. Therefore, rather than using the oxygen concentration test chip 1 and the oxygen concentration sensor 11, the present invention can be worked using an oxygen presence detection chip and an oxygen presence detection sensor that detect the presence of oxygen.

The detecting element pertaining to a first aspect of the present invention detects a parameter for a predetermined gas or liquid in a surrounding atmosphere by being excited by excitation light and generating light corresponding to the surrounding atmosphere, the detecting element including: a substrate; and nanoscale crystal structures formed on the substrate and constituted by a compound semiconductor light emitting element having a heterostructure well layer, wherein when the nanoscale crystal structures adsorb atoms or molecules of the predetermined gas or liquid, there is distortion of a band of a structure (material) with a smaller bandgap width in the well layer, this distortion brings about a change in transition energy (apparent bandgap width), and this change brings about a change in at least one of an intensity and a wavelength of light generated by the well layer, thereby indicating the parameter for the gas or the liquid.

The detecting element having this constitution is excited by excitation light and emits light corresponding to the surrounding atmosphere, and thereby detects a parameter (such as type, concentration, temperature, or humidity) for a predetermined gas or liquid in the surrounding atmosphere. The detecting element comprises nanoscale crystal structures that are formed on the substrate and are constituted by a compound semiconductor light emitting element having a heterostructure well layer. The nanoscale crystal structures are in the form of columns or sheets (walls), and at least the thinnest portion should be on the nanoscale. When the compound semiconductor light emitting element receives excitation light and emits light, if the nanoscale crystal structures adsorb atoms or molecules of the predetermined gas or liquid (the test substance), there will be distortion in the structure (material) with the smaller bandgap width in the well layer, this distortion will bring about a change in the transition energy (apparent bandgap width), and this change brings about a change in the intensity (brightness) and wavelength of light generated by the well layer. A specific parameter of the gas or liquid (test substance) is detected from a change in at least one of the intensity and the wavelength.

Because of their high growth temperature, the nanoscale crystal structures constituted by the compound semiconductor light emitting element can be used in high-temperature environments, and furthermore they are stable (undergo little corrosion or modification) with respect to many gases and liquids (test substances), so they can be used repeatedly. In particular, there is little degradation in sensitivity when the parameter is detected from the wavelength, so the detection is extremely quantitative and there is no need for calibration.

With the detecting element pertaining to a first aspect of the present invention, the light generated by the well layer can be set to a visible light region.

With this constitution, since the light from the detecting element is visible light, a person can easily ascertain by eye whether the test substance (the predetermined gas or liquid) is present, and its concentration.

With the detecting element pertaining to a first aspect of the present invention, the nanoscale crystal structures can be GaN nanocolumns having a well layer with a GaN/InGaN hetero structure.

With the detecting element pertaining to a first aspect of the present invention, the nanoscale crystal structures can have a basic unit with a column diameter of 100 nm and a triangular shape that is 230 nm on one side, and a length of the GaN nanocolumns is 1 μm.

The detecting device pertaining to a second aspect of the present invention detects a parameter for a predetermined gas or liquid, the detecting device including: a detecting element in which nanoscale crystal structures constituted by a compound semiconductor light emitting element having a heterostructure well layer are provided on a substrate; excitation means for causing the compound semiconductor light emitting element to emit light; and detection means for receiving the light emitted from the compound semiconductor light emitting element and detecting at least one of an intensity and a wavelength of this light, wherein when the nanoscale crystal structures adsorb atoms or molecules of the predetermined gas or liquid, there is distortion of a band of a structure (material) with a smaller bandgap width in the well layer, this distortion brings about a change in transition energy (apparent bandgap width), and the detection means detects a change in at least one of an intensity and a wavelength of light generated by the well layer, thereby detecting the parameter for the gas or the liquid.

With this constitution, with a detecting device that detects a specific parameter, such as the type, concentration, temperature, or humidity, for a gas or liquid (test substance), the detecting element comprises nanoscale crystal structures constituted by a compound semiconductor light emitting element having a heterostructure well layer. The nanoscale crystal structures are in the form of columns or sheets (walls), and at least the thinnest portion should be on the nanoscale. When the compound semiconductor light emitting element is excited by the excitation means and emits light, if the nanoscale crystal structures adsorb atoms or molecules of the predetermined gas or liquid (the test substance), there will be distortion in the structure (material) with the smaller bandgap width in the well layer, this distortion will bring about a change in the transition energy (apparent bandgap width), and this change brings about a change in the intensity (brightness) and wavelength of light generated by the well layer. The detection means detects at least one of these changes. At least one of the intensity and the wavelength is measured ahead of time and is then contrasted with the parameter for the predetermined gas or liquid (test substance), and the actual parameter value is calculated.

Because of their high growth temperature, the nanoscale crystal structures constituted by the compound semiconductor light emitting element can be used in high-temperature environments, and furthermore they are stable (undergo little corrosion or modification) with respect to many gases and liquids (test substances), so they can be used repeatedly. In particular, there is little degradation in sensitivity when the parameter is detected from the wavelength, so the detection is extremely quantitative and there is no need for calibration.

With the detecting device pertaining to a second aspect of the present invention, the nanoscale crystal structures can be GaN nanocolumns having a well layer with a GaN/InGaN heterostructure.

With the detecting device pertaining to a second aspect of the present invention, the nanoscale crystal structures can have a basic unit with a column diameter of 100 nm and triangular shape that is 230 nm on one side, and a length of the GaN nanocolumns is 1 μm.

With the detecting device pertaining to a second aspect of the present invention, the excitation means can be a light emitting element that optically excites the compound semiconductor light emitting element (using photoluminescence (PL)).

With the detecting device pertaining to a second aspect of the present invention, electrodes are attached to both ends of the nanoscale crystal structures, and the excitation means is a DC power supply.

With the detecting device pertaining to a second aspect of the present invention, the detection means can comprise at least three optical filters that disperse the light emitted from the compound semiconductor light emitting element, photodiodes that are provided corresponding to the optical filters and that detect an intensity of light that has passed through the corresponding optical filters, and computation means for computing a parameter value for the predetermined gas or liquid from an output of the photodiodes.

With this constitution, since the above-mentioned spectral distribution is used as a basis, the desired parameter value for a gas or liquid can be found very accurately.

With the detecting device pertaining to a second aspect of the present invention, the detecting device can further include a main body that is formed in a pen shape, and that has a pen tip at which the detecting element is provided, wherein the main body is provided with a remaining constitution and with display means for displaying a detection result of the detection means.

With this constitution, a portable type of detecting device can be obtained.

With the detecting device pertaining to a second aspect of the present invention, the detecting device can further include ultraviolet ray generating means at a cap that covers the pen tip.

With this constitution, the detecting element can be refreshed by using UV irradiation to scatter the molecules or atoms of the predetermined gas or liquid that have adsorbed to the detecting element.

The oxygen concentration test device pertaining to a third aspect of the present invention includes: a light emitting element that includes nanoscale crystal structures constituted by a compound semiconductor having a GaN/InGaN heterostructure well layer, and whose emission wavelength and brightness vary with an oxygen concentration in an atmosphere; a supply component that supplies excitation energy to the light emitting element; and a light receiving component that receives light emitted from the light emitting element by the excitation energy supplied from the supply component.

With this constitution, the oxygen concentration test device can be used in high-temperature environments. Here, the light emitting element corresponds to the oxygen concentration test chips 1 and 12 in the embodiments. The supply component corresponds to the UV light source 2 and the DC power supply 30 in the embodiments. The light receiving component corresponds to the photodiodes 33.

With the oxygen concentration test device pertaining to a third aspect of the present invention, the light emitting element further includes GaN layers sandwiching the well layer, and a structure constituted by the well layer and the GaN layers has a nanocolumn shape formed perpendicular to a substrate.

With this constitution, the surface area of the structures constituted by the well layer and the GaN layer can be increased, so a more sensitive oxygen concentration test device can be obtained.

With the oxygen concentration test device pertaining to a third aspect of the present invention, the nanoscale crystal structures can have a basic unit with a column diameter of 100 nm and a triangular shape that is 230 nm on one side, and a length of the nanocolumn is 1 μm.

With the oxygen concentration test device pertaining to a third aspect of the present invention, the oxygen concentration test device can further include an optical filter that is disposed along an optical path between the light emitting element and the light receiving component, and that disperses the light emitted from the light emitting element into three colors of red, blue, and green, wherein the light receiving component is divided into a red light receiving component that receives red light dispersed by the optical filter, a green light receiving component that receives green light dispersed by the optical filter, and a blue light receiving component that receives blue light dispersed by the optical filter, and the oxygen concentration test device further comprises a computer that computes the oxygen concentration on a basis of a spectral distribution found from outputs of the red light receiving component, the green light receiving component, and the blue light receiving component.

With this constitution, since the above-mentioned spectral distribution is used as a basis, the oxygen concentration can be found very accurately. Here, the unit constituted by the optical filter, the red light receiving component, the green light receiving component, and the blue light receiving component corresponds to a unit constituted by the red filters 32 and photodiodes 33, the green filters 32 and photodiodes 33, and the blue filters 32 and photodiodes 33 of this embodiment.

The invention claimed is:

1. A detecting element that detects a parameter for a predetermined gas or liquid in a surrounding atmosphere by being excited by excitation light and generating light corresponding to the surrounding atmosphere, the detecting element comprising:
    a substrate; and
    nanoscale crystal structures formed on the substrate and constituted by a compound semiconductor light emitting element having a heterostructure well layer,
    wherein when the nanoscale crystal structures adsorb atoms or molecules of the predetermined gas or liquid, there is distortion of a band of a structure with a smaller bandgap width in the well layer, this distortion brings about a change in transition energy, and this change brings about a change in at least one of an intensity and a wavelength of light generated by the well layer, thereby indicating the parameter for the gas or the liquid.

2. The detecting element according to claim 1, wherein the light generated by the well layer is set to a visible light region.

3. The detecting element according to claim 1, wherein the nanoscale crystal structures are GaN nanocolumns having a well layer with a GaN/InGaN heterostructure.

4. The detecting element according to claim 3, wherein the nanoscale crystal structures have a basic unit with a column diameter of 100 nm and a triangular shape that is 230 nm on one side, and
    a length of the GaN nanocolumns is 1 μm.

5. A detecting device that detects a parameter for a predetermined gas or liquid, comprising:
    a detecting element in which nanoscale crystal structures constituted by a compound semiconductor light emitting element having a heterostructure well layer are provided on a substrate;
    excitation component for causing the compound semiconductor light emitting element to emit light; and
    detection component for receiving the light emitted from the compound semiconductor light emitting element and detecting at least one of an intensity and a wavelength of this light,
    wherein when the nanoscale crystal structures adsorb atoms or molecules of the predetermined gas or liquid, there is distortion of a band of a structure with a smaller bandgap width in the well layer, this distortion brings about a change in transition energy, and the detection component detects a change in at least one of an intensity and a wavelength of light generated by the well layer, thereby detecting the parameter for the gas or the liquid.

6. The detecting device according to claim 5, wherein the nanoscale crystal structures are GaN nanocolumns having a well layer with a GaN/InGaN hetero structure.

7. The detecting device according to claim 6, wherein the nanoscale crystal structures have a basic unit with a column diameter of 100 nm and a triangular shape that is 230 nm on one side, and
    a length of the GaN nanocolumns is 1 μm.

8. The detecting device according to claim 5, wherein the excitation component is a light emitting element that optically excites the compound semiconductor light emitting element.

9. The detecting device according to claim 5, wherein electrodes are attached to both ends of the nanoscale crystal structures, and
    the excitation component is a DC power supply.

10. The detecting device according to claim 5, wherein the detection component comprises
    at least three optical filters that disperse the light emitted from the compound semiconductor light emitting element,
    photodiodes that are provided corresponding to the optical filters, and that detect an intensity of light that has passed through the corresponding optical filters, and
    computation component for computing a parameter value for the predetermined gas or liquid from an output of the photodiodes.

11. The detecting device according to claim 5, further comprising a main body that is formed in a pen shape, and that has a pen tip at which the detecting element is provided,
    wherein the main body is provided with a remaining constitution and with display component for displaying a detection result of the detection component.

12. The detecting device according to claim 11, further comprising ultraviolet ray generating component at a cap that covers the pen tip.

* * * * *